United States Patent [19]

Ohi et al.

[11] Patent Number: 4,911,759
[45] Date of Patent: Mar. 27, 1990

[54] DENTAL GYPSUM COMPOSITIONS IN LOW-DUSTING POWDERY FORM

[75] Inventors: Nobukazu Ohi, Fuchu; Hiroshi Kamohara, Kanamachi; Shunichi Futami, Nagareyama, all of Japan

[73] Assignee: G-C Dental Industiral Corporation, Tokyo, Japan

[21] Appl. No.: 233,916

[22] Filed: Aug. 18, 1988

Related U.S. Application Data

[63] Continuation of Ser. No. 20,582, Feb. 19, 1987, abandoned.

[30] Foreign Application Priority Data

Mar. 12, 1986 [JP]    Japan ............................ 61-52623

[51] Int. Cl.⁴ ........................ A61C 9/00; B28B 7/34; C04B 24/00
[52] U.S. Cl. ........................ 106/111; 106/35; 106/109; 106/110; 106/116; 433/199.1; 433/213; 433/214
[58] Field of Search ................ 106/35, 109, 110, 111, 106/116, 38.3, 38.35; 433/214, 213, 199.1; 164/DIG. 4

[56]    References Cited

U.S. PATENT DOCUMENTS

| | | | |
|---|---|---|---|
| 3,850,870 | 11/1974 | Kanakami et al. | 523/109 |
| 3,947,285 | 3/1976 | Jones et al. | 106/109 |
| 3,966,479 | 6/1976 | Koblitz | 106/109 |
| 4,268,310 | 5/1981 | Nemeth | 106/35 |
| 4,298,394 | 11/1981 | Leeming et al. | 106/111 |
| 4,394,172 | 7/1983 | Scheuble et al. | 106/35 |
| 4,526,619 | 7/1985 | Ohi et al. | 106/109 |
| 4,543,372 | 9/1985 | Watanabe et al. | 433/214 |
| 4,670,053 | 6/1987 | Kooke et al. | 106/209 |

FOREIGN PATENT DOCUMENTS 59-17065  4/1984  Japan.

Primary Examiner—Prince E. Willis
Assistant Examiner—Linda D. Skaling
Attorney, Agent, or Firm—Oblon, Spivak, McClelland, Maier & Neustadt

[57]    ABSTRACT

A dental gypsum composition in the low-dusting powdery form contains (a) hemihydrate gypsum, (b) a setting controlled agent comprising one or more of setting accelerators, setting retarders and setting expansion inhibitors, (c) one or more wetting agents selected from the group consisting of liquid hydrophobic hydrocarbons, liquid hydrophobic fatty acid esters and liquid hydrophobic fatty acids showing a vapor pressure of 3.15 mmHg or below at 20° C., and (d) one or more anionic surface active agents selected from the group consisting of alkylbenzene sulfonates and alkyl sulfates.

10 Claims, No Drawings

DENTAL GYPSUM COMPOSITIONS IN LOW-DUSTING POWDERY FORM

This application is a continuation of application Ser. No. 07/020,582, filed on Feb. 19, 1987, now abandoned.

BACKGROUND OF THE INVENTION

The present invention relates to a dental gypsum composition in the powdery form, which is used as the materials for models, denture investment and the like in the dental field.

STATEMENT OF THE PRIOR ART

Hitherto, when various restoration materials to be placed in the oral cavity have been prepared, dental gypsum compositions have been widely used as the important materials for the models therefor. For instance, they have been employed as the model materials for the preparation of working or jaw models and as the wax denture investment materials for the preparation of resin plates.

Such dental gypsum compositions contain as the main components alpha ($\alpha$)-hemihydrate gypsum (stone) and/or beta ($\beta$)-hemihydrate gypsum (plaster) to which a setting controlled agent is added, and such have been on the market in the powdery form.

In use, an operator charges and kneads the predetermined amounts of the dental powdery gypsum composition and water in a small bowl made of rubber with the use of a plaster spatula to form a gypsum slurry. Thereafter, when it is intended to use that slurry as the model material, it is poured into a negative mold obtained by impression taking from the oral cavity, and solidify therein, so a working or jaw model is prepared. When it is intended to use that slurry as the denture investment material, it is poured in a resin polymerization flask, and is cured therein for denture investment. Since such a dental gypsum composition in the powdery form is in a dried state, so that it takes long time for water to infiltrate thereinto and give moisture thereto, dusting takes place when it is mixed with water in a small bowl made of rubber by kneading with a plaster spatula to form a gypsum slurry. The resulting dust poses a problem in view of environmental health due to its irritation and harmfulness to the human body, which is pointed out to be one of the disadvantages of the dental gypsum compositions in the powdery form.

To eliminate this defect, Japanese Patent Publication No. 59-17065 proposes to reduce or limit dusting of dental gypsum compositions in the powdery form by adding an anhydrous wettable substance to hemihydrate gypsum. According to the teachings of Japanese Patent Publication No. 59-17065, the anhydrous wettable substances used include polyhydric alcohols represented by ethylene glycol, propylene glycol, glycerin and ethyl cellosolve.

Due their easy and rapid wetting properties, however, the anhydrous wettable substances disclosed in Japanese Patent Publication No. 59-17065 tend to increase the hygroscopic degree of the dental gypsum compositions in the powdery form. This does not only pose a grave problem in connection with the storage stability of such powders due to the fact that their quality degrades rapidly and, hence, their period of storage and use shorten considerably, but also offer a grave problem that the wet compressive strength of the solidified dental gypsum drops markedly. For these reasons, the dental powdery gypsum compositions still posing a dusting problem have generally been put in a wide use.

SUMMARY OF THE INVENTION

With the foregoing in mind, the present inventors have made extensive and intensive studies for the purpose of developing a dental gypsum composition in the powdery form, which does not give rise to the occurrence of dusting use, does not undergo any quality degradation during storage—this means that it excels in storage stability, and, once solidified, shows no sign of any lowering of compressive strength. As a result, it has been found that the aforesaid object is achieved by allowing one or more wetting agents selected from the group consisting of liquid hydrophobic hydrocarbons, liquid hydrophobic fatty acid esters and liquid hydrophobic fatty acids and one or more anionic surface active agents selected from the group consisting of alkylbenzene sulfonates and alkyl sulfates to be coexistent with a dental gypsum composition in the powdery form, said composition comprising hemihydrate gypsum and a setting controlled agent.

More specifically, the dental gypsum compositions in the low-dusting powdery form, according to the present invention, have improved low-dusting properties and storage stability by permitting at least one wetting agent selected from the group consisting of liquid hydrophobic hydrocarbons, liqid hydrophobic fatty acid esters and liquid hydrophobic fatty acids, all showing a vapor pressure of 3.15 mm Hg or below at 20° C. and at least one specific anionic surface active agent selected from the group consisting of alkyl sulfates and alkylbenzene sulfonates to coexist with a dental powdery gypsum composition comprising known components alpha ($\alpha$)-hemihydrate gypsum and/or beta ($\beta$)-hemihydrate gypsum and a setting controlled agent.

DETAILED DESCRIPTION OF THE INVENTION

In what follows, the present invention will be explained in more detail with reference to its preferred but non-restrictive embodiments.

Hemihydrate gypsum provides a main constituent of the dental gypsum composition in the low-dusting powdery form. The compressive strength of the solidified dental gypsum is considerably affected by a water-kneading ratio. In other words, the lower the water-kneading ratio, the higher the compressive strength attained. Where strength is required as is the case with the model materials, a large amount of alpha ($\alpha$)-hemihydrate gypsum of low water-kneading ratio is used. Where suitable strength and crushability are required as is the case with the denture investment materials, a large amount of beta ($\beta$)-hemihydrate gypsum of high water-kneading ratio is used.

As mentioned above, the dental powdery gypsum compositions find a great deal of use in dentistry, and it is of the most importance that the weight of powder and the volume of water be accurately weighed in order to achieve the suitable manipulation properties, viz., setting time, consistency and compressive strength, although they may vary according to the purpose. If the consistency of the compositions increase during storage, it is then impossible to obtain any proper compressive strength.

The setting controlling agent is used to afford the suitable manipulation properties and physical properties for the purpose intended to the dental gypsum compositions in the low-dusting powdery form. As the setting accelerators use may be made of inorganic acid salts such as NaCl or $K_2SO_4$ or known ones such as finely divided dihydrate gypsum. The setting retarders used include known ones comprising water-soluble high-molecular compound such as citrates, borates, carboxylates, acetates, starch, gum arabic, carboxymethyl cellulose or gelatin. Furthermore, the setting-expansion inhibitors used include known ones comprising soluble potassium salts such as potassium sulfate, potassium chloride or potassium tartrate. It is noted that known coloring agents and extenders may be added.

One wetting agent selected from the group consisting of liquid hydrophobic hydrocarbons, liquid hydrophobic fatty acid esters and liquid hydrophobic fatty acids, all showing a vapor pressure of 3.15 mmHg or below at 20° C. or a mixture of two or more thereof affords low-dusting properties to the dental powdery gypsum compositions and serve to maintain the storage stability thereof. However, since the wetting agents show a touch of oily nature for reasons of hydrophobic characteristics and causes a lowering of the efficiency of kneading manipulation, it needs be coexistent with a specific surface active agent.

Referring to the concrete examples of the substances used to wet powder particles, they have one or more wetting agents selected from the group consisting of liquid hydrophobic hydrocarbons, liquid hydrophobic fatty acid esters and liquid hydrophobic fatty acids, all showing a vapor pressure of 3.15 mmHg or below at 20° C.

The liquid hydrophobic hydrocarbons to be used include pristane, squalane, liquid paraffin, alpha ($\alpha$)-olefin oligomer, nonane, decane, undecane, dodecane, tridecane and so on.

The liquid hydrophobic fatty acid esters to be used include isopropyl palmitate, hexyl laurate, isopropyl myristate, isopropyl isostearate, butyl stearate, ethyl linoleate, isopropyl linoleate, ethyl olive-oleate, cetyl isooctanate, hexyldecyl myristate, hexyldecyl stearate, isostearyl palmitate, hexyldecyl isostearate, octyldodecyl neodecanoate, diethyl sebacate, diisopropyl sebacate, diisopropyl adipate and so on.

The liquid hydrophobic fatty acids to be used include isostearic acid, oleic acid, linolenic acid, linoleic acid, 2-ethylpentanoic acid, 2-ethylhexanoic acid and so on.

The anionic surface active agent is a component that is effective for removing a touch of oily nature from the aforesaid wetting agents and thereby improving the efficiency of kneading manipulation, and needs be coexistent with the wetting agents.

One or more anionic surface active agents should be selected from the group consisting of alkyl sulfates and alkylbenzene sulfonates. Nonionic surface active agents should be added in larger amounts so as to remove a touch of oily nature of liquid hydrophobic hydrocarbons, liquid hydrophobic fatty acids esters and liquid hydrophobic fatty acids. They also tend to lower the compressive strength of the solidified dental gypsum. Compared with the nonionic surface active agents, the alkyl sulfates and alkylbenzene sulfonates that are the anionic surface active agents can remove a touch of oily nature of the liquid hydrophobic hydrocarbons, liquid hydrophobic fatty acid esters and liquid hydrophobic fatty acids in smaller amounts and do not give rise to any lowering of wet compressive strength. This is because they are particularly preferable.

The akyl sulfates used as the anionic surface active agents may include sodium lauryl sulfate, potassium lauryl sulfate, sodium myristyl sulfate, sodium cetyl sulfate, sodium stearyl sulfate and so on. As the alkylbenzene sulfonates use may be made of sodium dodecylbenzene sulfonate and so on.

To permit the wetting agents and the anionic surface active agents to prevent the gypsum powders from dusting and to be used as a part of dental gypsum, it is preferred that one or more wetting agents selected from the group consisting of liquid hydrophobic hydrocarbons, liquid hydrophobic fatty acid esters and liquid hydrophobic fatty acids are added in an amount ranging from 0.5 to 5.0% by weight, one or more anionic surface active agents selected from the group consisting of alkylbenzene sulfonates and alkyl sulfates in an amount ranging from 0.01 to 0.5% by weight and the setting controlled agent is done in an amount of 0.05 to 5.0% by weight, although varying depending upon the particle size of the gypsum powders and the type of the surfactants used. If the wetting agent is used in an amount of below 0.5% by weight, then it has no effect upon preventing the gypsum powders from dusting. However, if the wetting agent is used in an amount exceeding 5.0% by weight, then the hydration reaction of gypsum is inhibited, resulting in a lowering of its wet compressive strength. If the anionic surface active agent is used in an amount of below 0.01% by weight, it is then impossible to remove a touch of oily nature from the wetting agent. On the other hand, when the anionic surface active agent is used in an amount exceeding 0.5% by weight, there are observed noticeable drops in degassing properties during mixing, storage stability and wet compressive strength. Further, if the setting controlled agent is used in an amount of below 0.05% by weight, it is then impossible to attain any appropriate setting time and setting expansion needed in dentistry. When used in an amount exceeding 5.0% by weight, on the other hand, it inhibits the hydration reaction with gypsum, and gives dental gypsum having considerably limited properties.

Of the liquids suitably used as the wetting agents for carrying out the present invention, nonane shows the highest vapor pressure 3.15 mm Hg at 20° C. Use of a liquid having a higher vapor pressure is unpreferred, since its content decreases gradually due to volatilization during storage. This is the reason why the vapor pressure is limited to 3.15 mm Hg or below in the present invention.

The dental gypsum compositions in the low-dusting powdery form according to the present invention can comfortably be used with no fear of environmental pollution, since they are substantially free from dusting, when they are carried to a storage vessel, weighed or mixed. Furthermore, the compositions according to the present invention have considerably improved storage stability and show stable manipulation properties and physical properties even after storage.

The present invention will now be further concretely explained with reference to examples. It is understood, however, that such examples are given by way of illustration alone, and not placing any limitation upon the wetting agents and anionic surface active agents used for carrying out the present invention.

EXAMPLES

In the respective examples and comparison examples, mixtures of alpha ($\alpha$)-and/or beta ($\beta$)-hemihydrate gypsum with one or more of the setting accelerator, setting retarder and setting expansion inhibitor used as the setting controlled agent was employed. The specified amount of the starting materials were placed in a blender for 15-minute blending. Blending was further continued with the dropwise addition, into the blender, of the prescribed amounts of one or more wetting agents selected from the group consisting of liquid hydrophobic hydrocarbons, liquid hydrophobic fatty acid esters and liquid hydrophobic fatty acids having a vapor pressure of up to 3.15 mm Hg or below at 20° C. and one or more anionic surface active agents selected from the group consisting of alkylbenzene sulfonates and alkyl sulfates. Mixing was afterwards continued for further 20 minutes, followed by screening with a 60 mesh sieve. Use was made of the powders which passed through that sieve.

The amount of water to be used in the preparation of the samples were determined according to the testing procedures of the Japanese Industrial Standards JIS T 6605 "Dental Stone". One hundred (100) grams of each sample was kneaded in varied amounts of water at a kneading rate of 100 revolutions per minute for 60 seconds, using a kneading bowl and a spatula usually employed for kneading in dentistry. Ten (10) ml of the kneaded product were weighed out with a glass tube having a diameter of 20 mm, and were thereafter gently forced out on a glass plate. Two (2) minutes after the start of kneading, a total weight of 120 g of a glass plate and a weight were placed thereon. Measurement was made of the maximum and minimum dimensions between the parallel lines defined by the thus spread sample. The standard consistency was then defined in terms of an average value of between 39 mm and 41 mm. The amount of water to be added was determined on the basis of an amount of water providing that standard consistency. This test was performed at room temperature of 15° to 20° C.

The setting time was determined according to the setting time testing of JIS T 6605 "Dental Stone". Each sample kneaded to the standard consistency was filled in a metal-made cylindrical mould of 20 mm in inner diameter and 30 mm in height, and a 300 gf loaded Vicat needle (having a diameter of 2 mm) was repeatedly stuck thereinto. The setting time was then expressed in terms of a period from the time of start of kneading with water to the time at which a sticking depth reached 1 mm. Wet compressive strength test was carried out according to the wet compressive strength testing of JIS T 6605. Each sample kneaded to the standard consistency was filled in a metal-made cylindrical mold of 20 mm in diameter and 30 mm in height and left at room temperature after being taken out of the mold, when solidified. Wet compressive strength was then determined by the crushing at a loading rate of 1 mm/min. using a compression testing machine after three hours from the time of start of kneading with water.

The storage stability was determined according to the accelerated aging testing wherein a polyethylene bag filled therein with each sample was stored for 60 days in a constant-temperature and humidity vessel maintained inside at a temperature of 37° C. and a humidity of 100%. After accelerated aging, measurement was made of the setting time and consistency of the sample. The storage stability was then expressed in terms of a delay time in minute and an increased consistency in mm obtained by subtracting the setting time and consistency predetermined before accelerated aging by the same procedures from the aforesaid measurements.

The low-dusting properties were estimated on the basis of the weight concentration of dust. Two hundreds (200) grams of each sample were charged in a metal-made cylindrical can ($\phi 150 \times 160$ mm), which was in turn vertically shaken five times at a rate of one reciprocation per second, immediately followed by encapping. The measurement of dust released from within the can was initiated with a digital type dust meter P-3 (manufactured by Shibata Kagaku, Co., Ltd.), and was continued for 3 minutes to determine the weight concentration of dust. The results are set forth in the following table.

| Example and Comparison Example No. | Constituent Components | Weight % | Standard Amount of Water (ml)* | Setting Time Before Accelerated Aging | Setting Time After Accelerated Aging | Consistency Before Accelerated Aging (mm) | Consistency After Accelerated Aging (mm) | Storage Stability Time Lags | Storage Stability Increase In Consistency (mm) | Wet Compressive Strength (kgf/cm²) | Weight Concentration Of Dust Powder (mg/m³) |
|---|---|---|---|---|---|---|---|---|---|---|---|
| 1 Example | α-CaSO₄.1/2H₂O<br>Squalane<br>Sodium lauryl sulfate<br>Setting controlled agent<br>(Potassium tartrate 0.1<br>Sodium citrate 0.5) | 97.0<br>2.0<br>0.4<br>0.6 | 24 | 10'30" | 12'15" | 40.0 | 41.2 | 1'45" | 1.2 | 503 | 1.24 |
| 2 Example | α-CaSO₄.1/2H₂O<br>Isopropyl myristate<br>Sodium lauryl sulfate<br>Setting controlled agent<br>(Sodium citrate 0.6) | 97.0<br>2.0<br>0.4<br>0.6 | 24 | 10'45" | 12'45" | 40.5 | 41.4 | 2'00" | 0.9 | 512 | 1.29 |
| 3 Example | α-CaSO₄.1/2H₂O<br>Oleic acid<br>Sodium lauryl sulfate<br>Setting controlled agent<br>(K₂SO₄ 0.2<br>Gum arabic 0.4) | 97.0<br>2.0<br>0.4<br>0.6 | 24 | 10'30" | 12'30" | 39.8 | 41.8 | 2'00" | 2.0 | 508 | 1.26 |
| 4 Example | αCaSO₄.1/2H₂O<br>Squalane<br>Sodium lauryl sulfate<br>Setting controlled agent<br>(Borax 0.5) | 98.95<br>0.5<br>0.05<br>0.5 | 24 | 10'45" | 12'45" | 40.4 | 42.3 | 2'00" | 1.9 | 525 | 2.03 |
| 5 Example | α-CaSO₄.1/2H₂O<br>Liquid paraffin<br>α-olefin oligomer<br>Sodium dodecylbenzene sulfonate<br>Setting controlled agent<br>(Potassium tartrate 0.6) | 95.0<br>2.0<br>2.0<br>0.4<br>0.6 | 24 | 10'15" | 12'15" | 41.3 | 42.1 | 2'00" | 0.8 | 487 | 1.03 |
| 6 Example | β-CaSO₄.1/2H₂O<br>Isopropyl isostearate<br>Sodium dodecylbenzene sulfonate<br>Setting controlled agent<br>(Finely divided dihydrated gypsum 0.6) | 96.3<br>2.6<br>0.5<br>0.6 | 50 | 10'15" | 12'15" | 39.1 | 40.3 | 2'00" | 1.2 | 105 | 1.30 |
| 7 Example | β-CaSO₄.1/2H₂O<br>2-ethylpentanoic acid<br>Sodium lauryl sulfate<br>Setting controlled agent<br>(Sodium gluconate 0.6) | 96.3<br>2.6<br>0.5<br>0.6 | 50 | 10'45" | 12'30" | 39.5 | 40.5 | 1'45" | 1.0 | 107 | 1.25 |

-continued

| Example and Comparison Example No. | | Constituent | | Standard Amount of Water (ml)* | Setting Time Before Accelerated Aging | Setting Time After Accelerated Aging | Consistency Before Accelerated Aging (mm) | Consistency After Accelerated Aging (mm) | Storage Stability | | Wet Compressive Strength (kgf/cm²) | Weight Concentration Of Dust Powder (mg/m³) |
|---|---|---|---|---|---|---|---|---|---|---|---|---|
| | | Components | Weight % | | | | | | Time Lags | Increase In Consistency (mm) | | |
| 8 | Example | α-CaSO₄.1/2H₂O<br>β-CaSO₄.1/2H₂O<br>Isopropyl linolate<br>Sodium lauryl sulfate<br>Sodium dodecylbenzene sulfonate<br>Setting controlled agent<br>$\left(\begin{array}{ll}K_2SO_4 & 0.3 \\ \text{Potassium tartrate} & 0.2 \\ \text{Sodium citrate} & 0.1\end{array}\right)$ | 48.2<br>48.2<br>2.6<br>0.2<br>0.2<br>0.6 | 38 | 10'30" | 12'30" | 39.5 | 40.4 | 2'00" | 0.9 | 187 | 1.27 |
| 9 | Example | αCaSO₄.1/2H₂O<br>β-CaSO₄.1/2H₂O<br>Linolenic acid<br>Liquid paraffin<br>Sodium myristyl sulfate<br>Setting controlled agent<br>(Carboxymethyl cellulose 0.6) | 48.2<br>48.2<br>1.3<br>1.2<br>0.5<br>0.6 | 38 | 10'45" | 12'45" | 40.5 | 41.9 | 2'00" | 1.4 | 195 | 1.26 |
| 10 | Comparison Example | α-CaSO₄ 1/2H₂O<br>Setting controlled agent<br>$\left(\begin{array}{ll}\text{Potassium tartrate} & 0.1 \\ \text{Sodium citrate} & 0.5\end{array}\right)$ | 99.4<br>0.6 | 24 | 10'30" | 16'45" | 39.0 | 49.7 | 6'15" | 10.7 | 485 | 6.32 |
| 11 | Comparison Example | β-CaSO₄ 1/2H₂O<br>Setting controlled agent<br>(Finely divided dihydrated gypsum 0.6) | 99.4<br>0.6 | 50 | 10'15" | 17'00" | 40.2 | 50.6 | 6'45" | 10.4 | 93 | 6.78 |
| 12 | Comparison Example | α-CaSO₄.1/2H₂O<br>β-CaSO₄.1/2H₂O<br>Setting controlled agent (K₂SO₄ 0.6) | 49.7<br>49.7<br>0.6 | 38 | 10'15" | 16'15" | 39.4 | 51.6 | 6'00" | 12.2 | 180 | 6.48 |
| 13 | Comparison Example | α-CaSO₄.1/2H₂O<br>Propylene glycol<br>Setting controlled agent (Borax 0.6) | 96.9<br>2.5<br>0.6 | 24 | 10'30" | 21'00" | 40.0 | 55.0 | 10'30" | 15.0 | 405 | 1.24 |
| 14 | Comparison Example | α-CaSO₄.1/2H₂O<br>β-CaSO₄.1/2H₂O<br>Ethylene glycol<br>Setting Controlled agent (Sodium gluconate 0.5) | 48.5<br>48.5<br>2.5<br>0.5 | 38 | 10'15" | 21'45" | 40.5 | 55.8 | 11'30" | 15.3 | 113 | 1.25 |

*The standard amount of ml of water to be used is in amount to 100 g powder.

EFFECT OF THE INVENTION

In the compositions of Comparison Examples 10, 11, 12, 13 and 14 wherein use was not made of one or more wetting agents selected from the group consisting of the liquid hydrophobic hydrocarbons, liquid hydrophobic fatty acid esters and liquid hydrophobic fatty acids and the specific one or more anionic surface active agents selected from the group consisting of alkylbenzene sulfonates and alkyl sulfates, the weight concentration of dust did all exceeded 6.32 mg/m$^3$. This implies that, with such compositions, there is a possibility that environmental pollution may take place due to dusting. In the compositions of Examples 1 to 5 and 7 to 9 wherein the specific wetting and anionic surface active agents were added, the weight concentration of dust was all decreased to up to 2.03 mg/m$^3$.

Further referring to the storage stability (expressed in terms of a difference between the setting time before accelerated aging and the setting time after accelerated aging and a difference between the consistency before accelerated aging and the consistency after accelerated aging), Comparison Examples 10, 11, 12, 13 and 14, wherein the aforesaid wetting and anionic surface active agents were not added at all, showed setting time lags of 6 minutes 15 seconds, 6 minutes 45 seconds, 6 minutes 00 seconds, 10 minutes 30 seconds and 11 minutes 30 seconds, respectively, whereas Examples 1 to 9 inclusive, wherein the wetting and anionic surface active agents were added in the specific proportions, each showed a setting time lag of within 2 minutes. Turning to the consistency, the compositions of Comparison Examples 10 to 14 inclusive, wherein the wetting and anionic surface active agents were not added at all, had their consistency increased to 10.7 mm, 10.4 mm, 12.2 mm, 15.0 mm and 15.3 mm, respectively, whereas the compositions of Examples 1 to 9 inclusive, wherein the wetting and anionic surface active agents were added in the specific proportions, each showed an increase of within 2.0 mm; this means that their storage stability was extremely improved.

The composition of Comparison Example 10, wherein alpha ($\alpha$)-hemihydrate gypsum was used as the main component, and the wetting and anionic surface active agents were not added at all, showed a wet compressive strength of 485 Kgf/cm$^2$, whereas the composition of Example 1, 2, 3, 4 or 5, wherein the same main component was used, and the wetting and anionic surface active agents were added in the specific proportions, showed a wet compressive strength of 503 Kgf/cm$^2$, 512 Kgf/cm$^2$, 508 Kgf/cm$^2$, 525 Kgf/cm$^2$ or 487 Kgf/cm$^2$. The composition of Comparison Example 11, wherein beta ($\beta$)-hemihydrate gypsum was used as the main component and the wetting and anionic surface active agents were not added at all, showed a wet compressive strength of 93 Kgf/cm$^2$, whereas the composition of Example 6 or 7, wherein the same main component was used, and the wetting and anionic surface active agents were added in the specific proportions, showed a wet compressive strength of 105 Kgf/cm$^2$ or 107 Kgf/cm$^2$. The composition of Comparison Example 12, wherein a mixture of alpha ($\alpha$)- and beta ($\beta$)-hemihydrate gypsum was used as the main component, and the wetting and anionic surface active agents were not added at all, showed a wet compressive strength of 180 Kgf/cm$^2$, whereas the composition of Example 8 or 9, wheren the same main component was used, and the wetting and anionic surface active agents were added in the specific proportions, exhibited a wet compressive strength of 187 Kgf/cm$^2$ or 195 Kgf/cm$^2$.

As explained in detail in the foregoing, the dental powdery gypsum compositions of the Comparison Examples, wherein any wetting and anionic surface active agents are not used, give rise to a fear of environmental pollution due to dusting and a lowering of storage stability due to a delay in their setting time and an increase in consistency after accelerated aging. It is found, however, that the inventive dental gypsum compositions in the low-dusting powdery form show little or no sign of dusting, excel in storage stability and little or no sign of a decrease in wet compressive strength. This indicates that the invented compositions have much more improved dental properties.

It is to be understood that while the present invention has been described with reference to the specific embodiments, many modifications or changes may be made without departing from the scope defined in the appended claims.

What is claimed is:

1. A low-dusting powder dental gypsum composition, consisting essentially of:
   (a) a hemihydrate gypsum;
   (b) 0.05 to 5.00 parts by weight of a setting controlling agent which is at least one member selected from the group consisting of inorganic acid salt setting accelerator, setting retarders, and setting expansion inhibitors;
   (c) 0.5 to 5.00 parts by weight of a wetting agent which is at least one member selected from the group consisting of liquid hydrophobic hydrocarbons, liquid hydrophobic fatty acid esters, isosteric acid, oleic acid, linolenic acid, linoleic acid, 2-ethylpentanoic acid, and 2-ethylhexanoic acid, wherein said wetting agent has a vapor pressure of 3.15 mm Hg or below at 20° C.; and
   (d) 0.01 to 0.50 parts by weight of an anionic surface active agent which is at least one member selected from the group consisting of alkylbenzene sulfonates and alkyl sulfates;
   wherein the total amount of components (a), (b), (c) and (d) adds up to 100 parts by weight.

2. The low-dusting powder dental gypsum composition of claim 1, wherein said setting controlling agent is a setting accelerator.

3. The low-dusting powder dental gypsum composition of claim 1, wherein said setting controlling agent is a setting retarder.

4. The low-dusting powder dental gypsum composition of claim 1, wherein said setting controlling agent is a setting inhibitor.

5. The low-dusting powder dental gypsum composition of claim 1, wherein said liquid hydrophobic hydrocarbon is one member selected from the group consisting of pristane, squalane, a liquid paraffin, an alpha-olefin oligomer, nonane, decane, undecane, dodecane and tridecane.

6. The low-dusting powder dental gypsum composition of claim 1, wherein said liquid hydrophobic fatty acid ester is one member selected from the group consisting of isopropyl palmitate, hexyl laurate, isopropyl myristate, isopropyl isostearate, butyl stearate, ethyl linoleate, isopropyl linoleate, ethyl olive-oleate, ctyl issooctanate, hexyldecyl myristate, hexyldecylstearate, isostearyl palmitate, hexyldecyl isostearate, octyldodecyl neodecanoate, diethyl sebacate, diisopropyl sebacate, and diisopropyl adipate.

7. The low-dusting powder dental gypsum composition of claim 1, wherein said anionic surface active agent is an alkylbenzene sulfonate.

8. The low-dusting powder dental gypsum composition of claim 1, wherein said anionic surface active agent is an alkyl sulfate.

9. The low-dusting powder dental gypsum composition of claim 1, wherein alkyl sulfate is one member selected from the group consisting of sodium lauryl sulfate, potassium lauryl sulfate, sodium myristyl sulfate, sodium cetyl sulfate, and sodium stearyl sulfate.

10. The low-dusting powder dental gypsum composition of claim 1, wherein said anionic surface active agent is sodium dodecylbenzene sulfonate.

* * * * *